(12) United States Patent
Altamura

(10) Patent No.: US 12,414,838 B2
(45) Date of Patent: Sep. 16, 2025

(54) SYSTEMS AND METHODS FOR RETRACTOR HOLDER

(71) Applicant: Altasurgical LLC, Union City, NJ (US)

(72) Inventor: Michael Altamura, Croton-on-Hudson, NY (US)

(73) Assignee: Altasurgical LLC, Union City, NJ (US)

( * ) Notice: Subject to any disclaimer, the term of this patent is extended or adjusted under 35 U.S.C. 154(b) by 231 days.

(21) Appl. No.: 18/085,965

(22) Filed: Dec. 21, 2022

(65) Prior Publication Data

US 2023/0218367 A1    Jul. 13, 2023

Related U.S. Application Data

(60) Provisional application No. 63/302,725, filed on Jan. 25, 2022, provisional application No. 63/297,930, filed on Jan. 10, 2022.

(51) Int. Cl.
*B25B 1/00*    (2006.01)
*A61B 90/57*   (2016.01)

(52) U.S. Cl.
CPC ........ *A61B 90/57* (2016.02); *A61B 2090/571* (2016.02)

(58) Field of Classification Search
CPC ....... B25B 1/22; B25B 1/2421; B25B 1/2457; B25B 3/00; B25B 1/06
See application file for complete search history.

(56) References Cited

U.S. PATENT DOCUMENTS

| | | | | |
|---|---|---|---|---|
| 4,119,305 A | * | 10/1978 | Anderson | B25B 1/22 269/238 |
| 4,214,739 A | * | 7/1980 | Dailey | B25B 1/22 269/75 |
| 5,165,673 A | * | 11/1992 | Newton, Jr. | A01K 97/28 269/69 |
| 5,775,679 A | * | 7/1998 | Strub | A01K 97/28 269/95 |
| 5,809,686 A | * | 9/1998 | Abby | A01K 97/28 269/69 |
| 5,826,867 A | * | 10/1998 | Roby | F16M 11/14 269/74 |
| 7,566,022 B1 | * | 7/2009 | McKinley | A01K 97/28 269/221 |
| 7,950,638 B2 | * | 5/2011 | Su | A01K 97/28 269/95 |
| 2009/0045310 A1 | * | 2/2009 | Koesema, Jr. | F16L 3/13 248/65 |
| 2023/0218367 A1 | * | 7/2023 | Altamura | A61B 90/57 600/227 |

* cited by examiner

*Primary Examiner* — Lee D Wilson
(74) *Attorney, Agent, or Firm* — Rothwell, Figg, Ernst & Manbeck, P.C.

(57) ABSTRACT

Systems and methods for a vaginal speculum holder are disclosed. In some aspects, a system may include a retractor and a holder. The retractor may include a blade assembly, a base, and one or more supports attached to the base and the blade assembly. In some aspects, the holder may include a receptacle configured to receive the base, and a fastener configured to secure the holder to an object. In some aspects, the method may include using a fastener of a holder to secure the holder to an object and using a receptacle of the holder to receive a base of a retractor.

22 Claims, 18 Drawing Sheets

SYSTEMS AND METHODS FOR RETRACTOR HOLDER

CROSS-REFERENCE TO RELATED APPLICATIONS

This application claims the benefit of priority to U.S. Provisional Application Ser. No. 63/302,725, filed Jan. 25, 2022, and U.S. Provisional Application Ser. No. 63/297,930, filed Jan. 10, 2022, which are incorporated herein by reference in their entireties.

FIELD OF INVENTION

The present disclosure relates generally to the field of medical tools and devices. More specifically, the present disclosure relates to systems and methods for a retractor holder and use thereof.

BACKGROUND

Retractors are medical instruments used to create space in a body (e.g., for visualization and/or access during examination and/or surgery). Surgical vaginal speculums are self-retaining retractors used to obtain exposure to the vaginal canal to permit vaginal surgery. The existing speculums are composed of a blade which is inserted into the vaginal canal and a stem or handle which may or may not incorporate a weight to cause depression of the posterior vaginal wall to create space. The length of the blade for each speculum is fixed for which reason the operating room has to have an array of speculums of different sizes to adjust for the depth of the vagina. Furthermore, the existing speculums have a fixed angle between the blade and the stem. Therefore, they are not always a proper fit corresponding to the pitch of the vagina which depends on the pliability of the posterior wall. This can affect the degree of exposure created by the speculum. Because the pitch of the vagina depends on the pliability of the posterior vaginal wall, the angled speculums, which are meant to be self-retaining, cannot be properly inserted in those cases where the vaginal canal has little or no pliability. In this case, a 90 degree angle speculum is used which requires an assistant to apply downward pressure on the blade, as these speculums do not incorporate a weight.

Existing retractors (e.g., speculums) use means such as a clamp to secure the retractor to an operating table. Other existing retractors just have a weight and are not attached to the operating table, which may cause the retractors to slip out of the vagina due the fixed blade length and fixed angle of the retractor.

SUMMARY

Clamps used to secure retractors (e.g., speculums) to operating tables can cause stability issues, particularly if the clamp is merely a general clamp and is not configured to hold the retractor to the table. Furthermore, a retractor that has been clamped to an operating table cannot generally be moved (e.g., side-to-side) relative to the operating site. Therefore, there exists a need for a holder for a retractor that is capable of both securing the retractor to an object (e.g., an operating table) while still enabling the retractor to be moved at least side-to-side by an operator.

Aspects of the invention may overcome one or more the problems associated with the existing solutions for securing retractors to objects (e.g., operating tables) by providing a retractor holder.

One aspect of the invention may provide a system including a retractor and a holder. The retractor may include a blade assembly, a base, and one or more supports attached to the base and the blade assembly. The holder may include a receptacle configured to receive the base and a fastener configured to secure the holder to an object.

In some aspects, the retractor may be a speculum. In some aspects, the object may be an operating room table. In some aspects, the one or more supports may include one or more columns.

In some aspects, the fastener may be a clip. In some aspects, the receptacle may include a sleeve. In some aspects, the receptacle may be made of plastic.

In some aspects, the receptacle may be configured to prevent rotation of the base about a longitudinal axis of the base. In some aspects, the holder may be configured to maintain the base of the retractor at a constant height. In some aspects, the holder may be configured to maintain a longitudinal axis of the one or more supports in a vertical orientation. In some aspects, the receptacle of the holder may be configured such that the base of the retractor is capable of side-to-side movement within the receptacle.

Another aspect of the invention may provide a holder including a receptacle configured to receive a base of a retractor and a fastener configured to secure the receptacle to an object.

In some aspects, the object may be an operating room table. In some aspects, the fastener may be a clip. In some aspects, the receptacle may include a sleeve.

In some aspects, the receptacle may be configured to prevent rotation of the base about a longitudinal axis of the base. In some aspects, the holder may be configured to maintain the base of the retractor at a constant height. In some aspects, the retractor may include one or more supports attached to the base, and the holder is configured to maintain a longitudinal axis of the one or more supports in a vertical orientation. In some aspects, the receptacle of the holder configured such that the base of the retractor is capable of side-to-side movement within the receptacle.

Still another aspect of the invention may provide a method. The method may include using a fastener of a holder to secure the holder to an object. The method may include using a receptacle of the holder to receive a base of a retractor.

In some aspects, the method further include moving the base of the retractor from one side of the receptacle to another side of the receptacle.

Further variations encompassed within the systems, holders, and methods are described in the detailed description below.

BRIEF DESCRIPTION OF THE DRAWINGS

The accompanying drawings, which are incorporated herein and form part of the specification, illustrate various, non-limiting aspects of the present invention. In the drawings, like reference numbers indicate identical or functionally similar elements.

PARTS LIST

Figure 1:
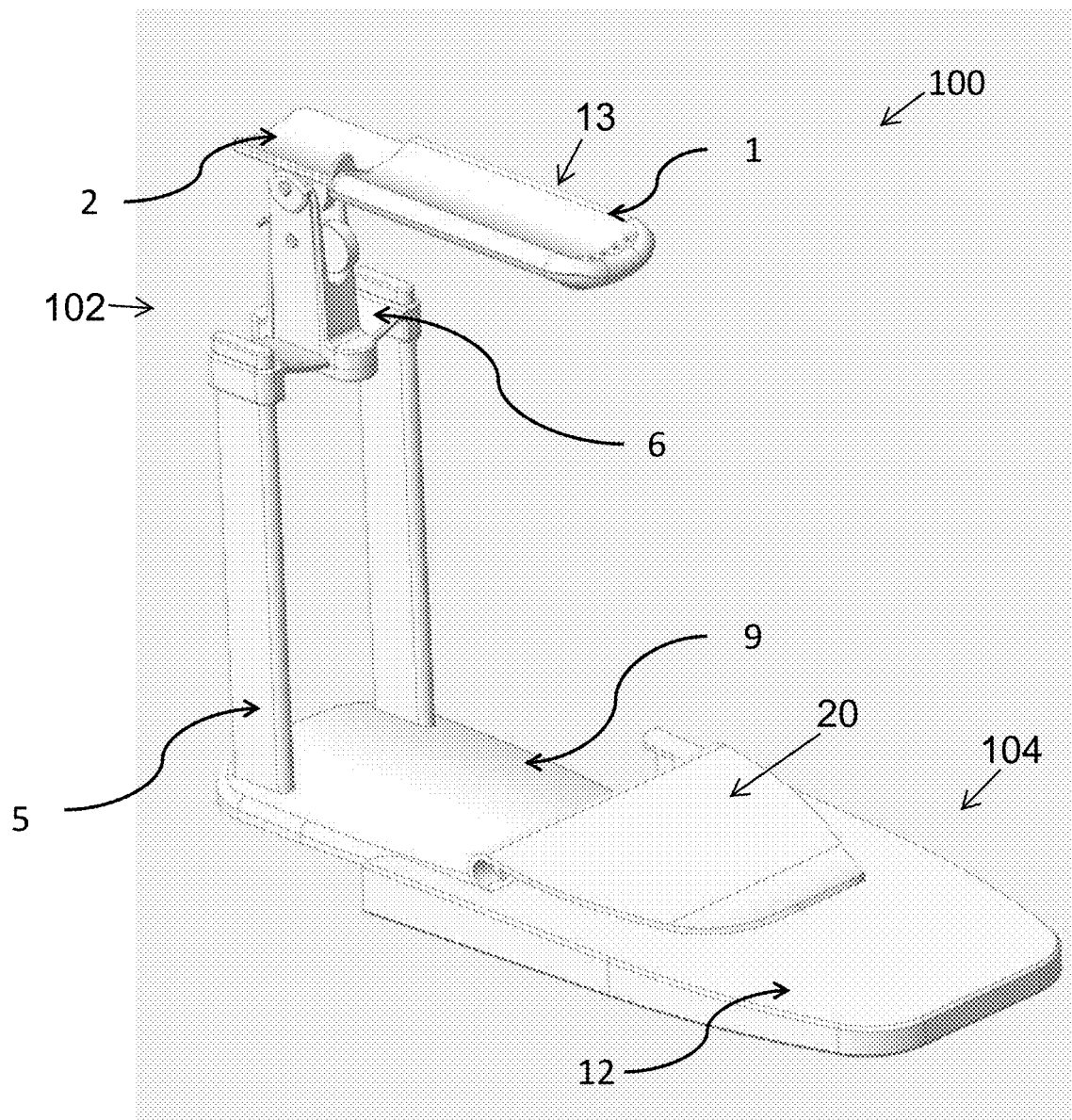
FIG. 1 shows an isometric view of an exemplary system wherein the retractor holder houses the base assembly, according to some aspects.

100. System
102. Retractor
104. Holder
1. Movable vacuum blade
2. Fixed blade
3. Spring loaded ratchet parts
4. Suction Plate
5. One or more supports
6. Slider
7. Slider track
8. Screws
9. Base
10. Suction Holes
11. Suction Connection
12. Receptacle
13. Blade Assembly
14. Ratchet Assembly
15. Base Assembly
16. Light Assembly
17. Pivot Connection
18. Support Structure
19. Pivoting Mechanism
20. Fastener

DETAILED DESCRIPTION

Figure 2:
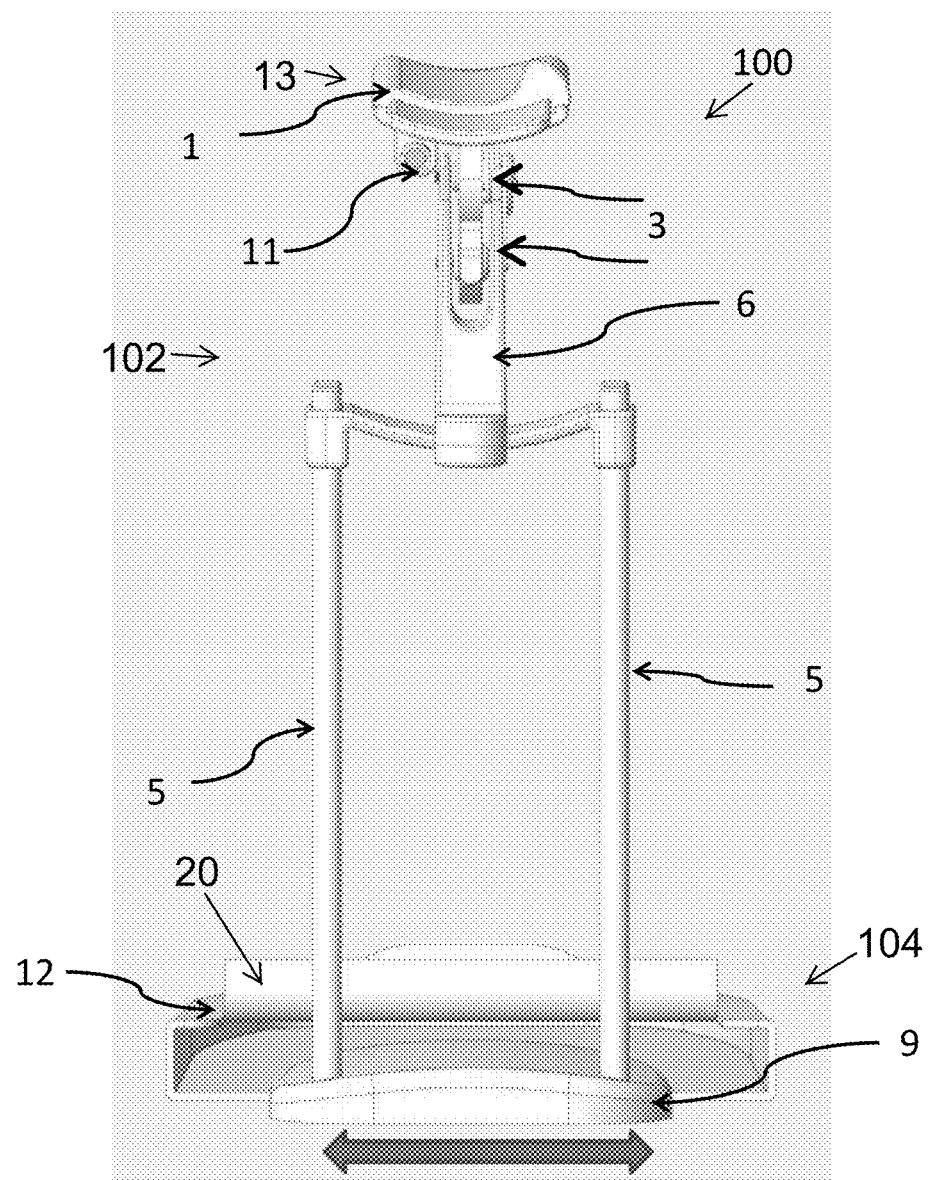
FIG. 2 shows a back view of an exemplary system wherein the base assembly indicates the side-to-side movement inside the retractor holder, according to some aspects.

FIGS. 1 and 2 illustrate a system 100 including a retractor 102 and a holder 104. In some aspects, the retractor 102 may be, for example and without limitation, a vaginal speculum. In some alternative aspects, the retractor 102 may be another type of retractor (e.g., a rectal speculum, a nasal speculum, or an ear speculum). In some aspects, as shown in FIG. 1, the retractor 102 may include a blade assembly 13. In some aspects, the blade assembly 13 may include a movable blade 1 and a fixed blade 2. In some aspects, the moveable blade 1 may glide over a fixed blade 2 (e.g., to adjust to the length of the vaginal canal of a patient undergoing surgery). In some aspects, the moveable blade 1 may be a vacuum sleeve. In some aspects, the retractor 102 may include a base 9, which may act as the fulcrum for the retractor 102.

In some aspects, as shown in FIGS. 1 and 2, the holder 104 may be fastened or otherwise attached to an object (e.g., an operating table). In some aspects, the holder 104 may allow for movement (e.g., side-to-side movement) of the base 9 in the holder 104 (e.g., for adjustment of the position of the retractor 102 relative to an operating site). In some aspects, the retractor holder 104 may include a receptacle 12 configured to receive and hold the base 9 of the retractor 102. In some aspects, the retractor holder 104 may also include a fastener 20. In some aspects, the fastener 102 may be configured to secure the holder 104 to an object (e.g., an operating table). In some aspects, as shown in FIGS. 1 and 2, the fastener 20 may be a clip. In some alternative aspects, a different structure (e.g., a bolt and nut, a screw, or a clamp) may be used for the fastener 20.

In some aspects, the holder 104 may be configured to maintain the base 9 of the retractor 102 at a constant height (e.g., relative to an operating site and/or the object) when the fastener 20 secures the holder 104 to the object and the base 9 of the retractor 102 is in the receptacle 12 of the holder 104. In some aspects, the holder 104 may additionally or alternatively be configured to maintain a longitudinal axis of one or more supports 5 of the retractor 102 in a vertical orientation. In some aspects, the receptacle 12 of the holder 104 may be configured to prevent rotation of the base 9 of the retractor 102 above a longitudinal axis of the base 9 (e.g., so that one or more supports 5 of the retractor 102 remains in a vertical orientation while the base 9 of the retractor 102 is in the receptacle 12 of the holder 104).

As further shown in at least FIG. 2, in some aspects, the retractor 102 may include spring-loaded ratchet parts 3 that allow for changing of the angle of the blade assembly 13 in an upward or downward direction. In some aspects, the spring-loaded ratchet parts 3 may allow the angle of the blade assembly 13 to be adjusted (e.g., so that it corresponds to the vaginal pitch and thereby gains as much exposure as possible). For example, the spring-loaded ratchet parts 3 may be adjusted so that it corresponds to the vaginal pitch and thereby gains as much exposure as possible. In some alternative aspects, other mechanisms to adjust an angle may be used.

Figure 3:
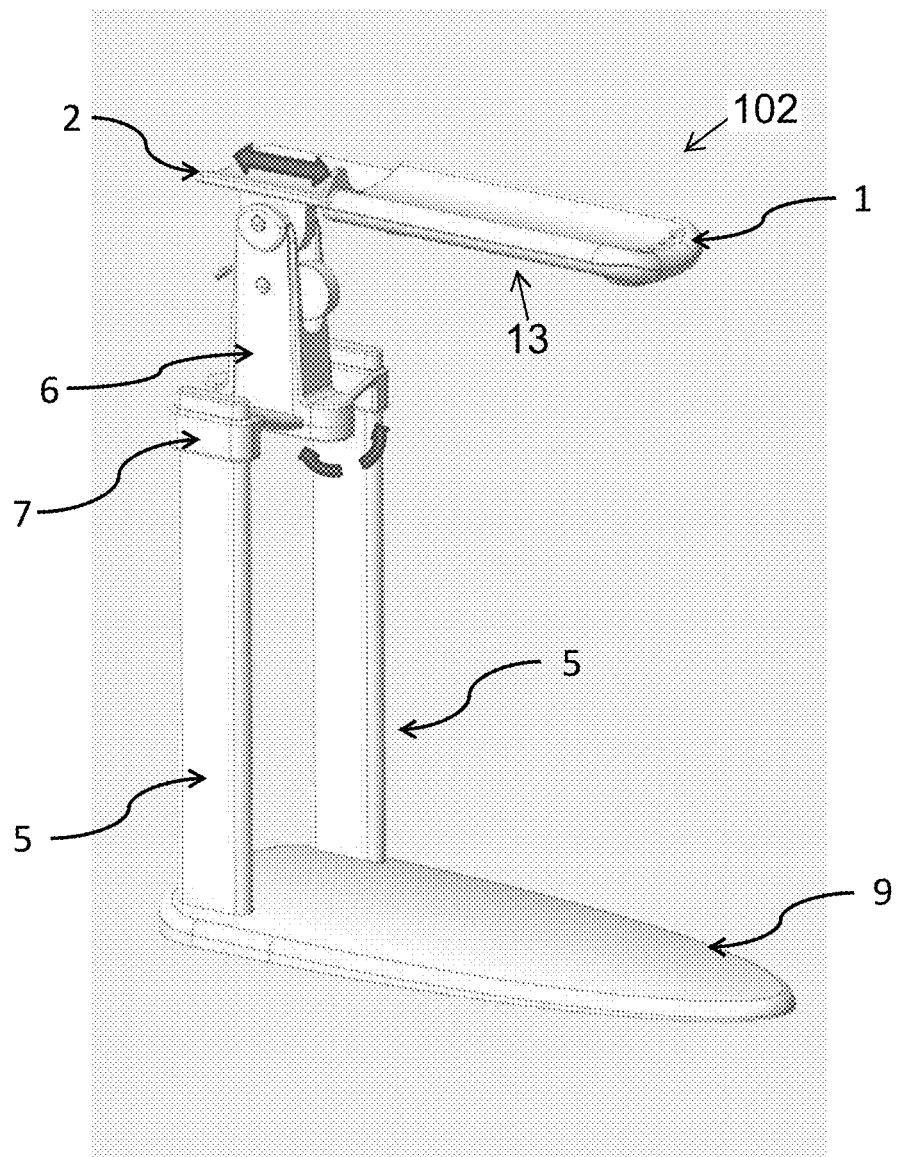
FIG. 3 shows an isometric view of an exemplary system wherein the blade is extended and at the top most position on the supports, according to some aspects.

FIGS. 3-14 further illustrate the retractor 102 according to some aspects. As shown in at least FIG. 3, in some aspects, the blade assembly 13 may be attached to a slider track 7 that allows rotation of the blade assembly 13 (e.g., at least 15 degrees to the right of the midline and at least 15 degrees to the left of the midline for the vertical position). FIG. 3 further shows, in some aspects, the sliding motion of the movable vacuum sleeve 1.

Figure 4:
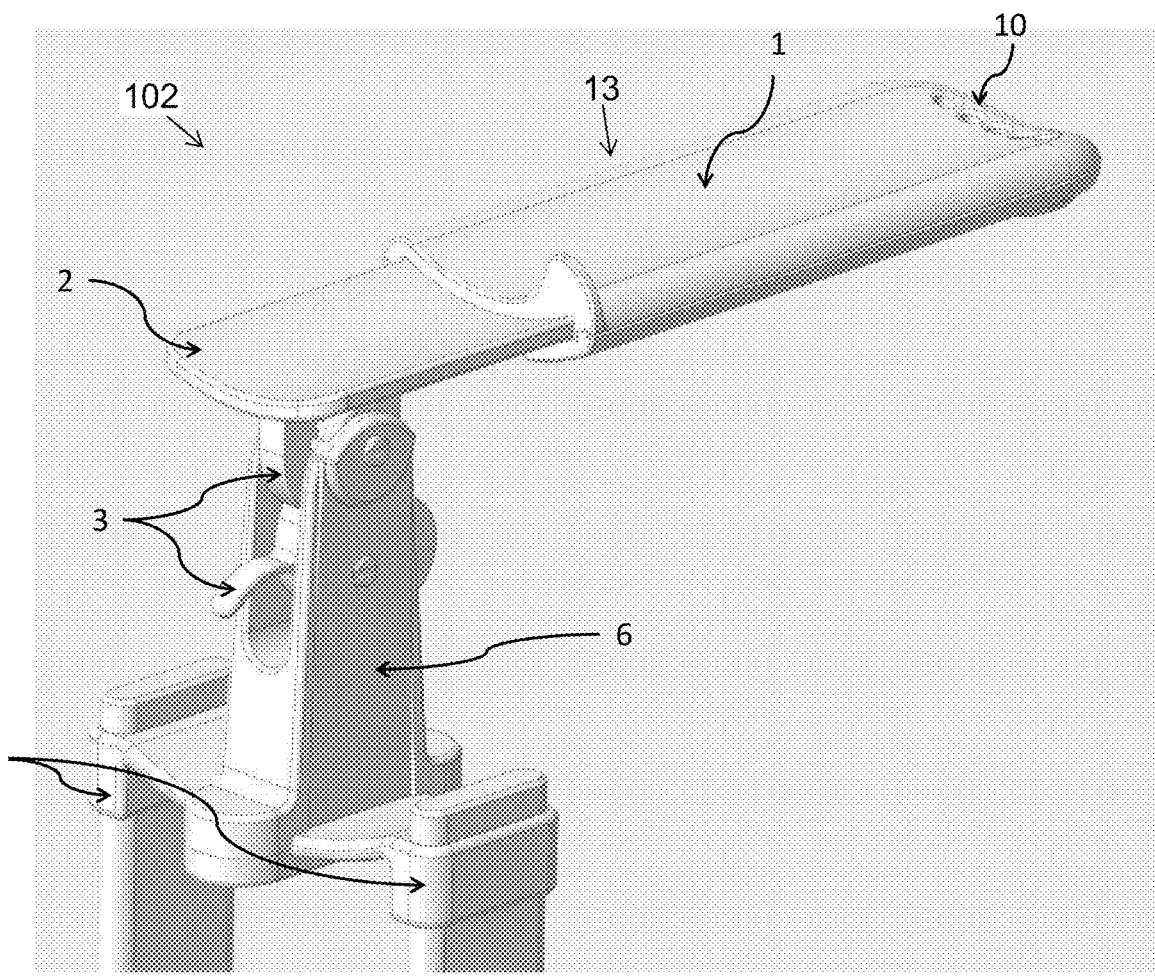
FIG. 4 shows a close-up isometric view of a system wherein the blade is extended and the ratchet back side in view, according to some aspects.
Figure 7:
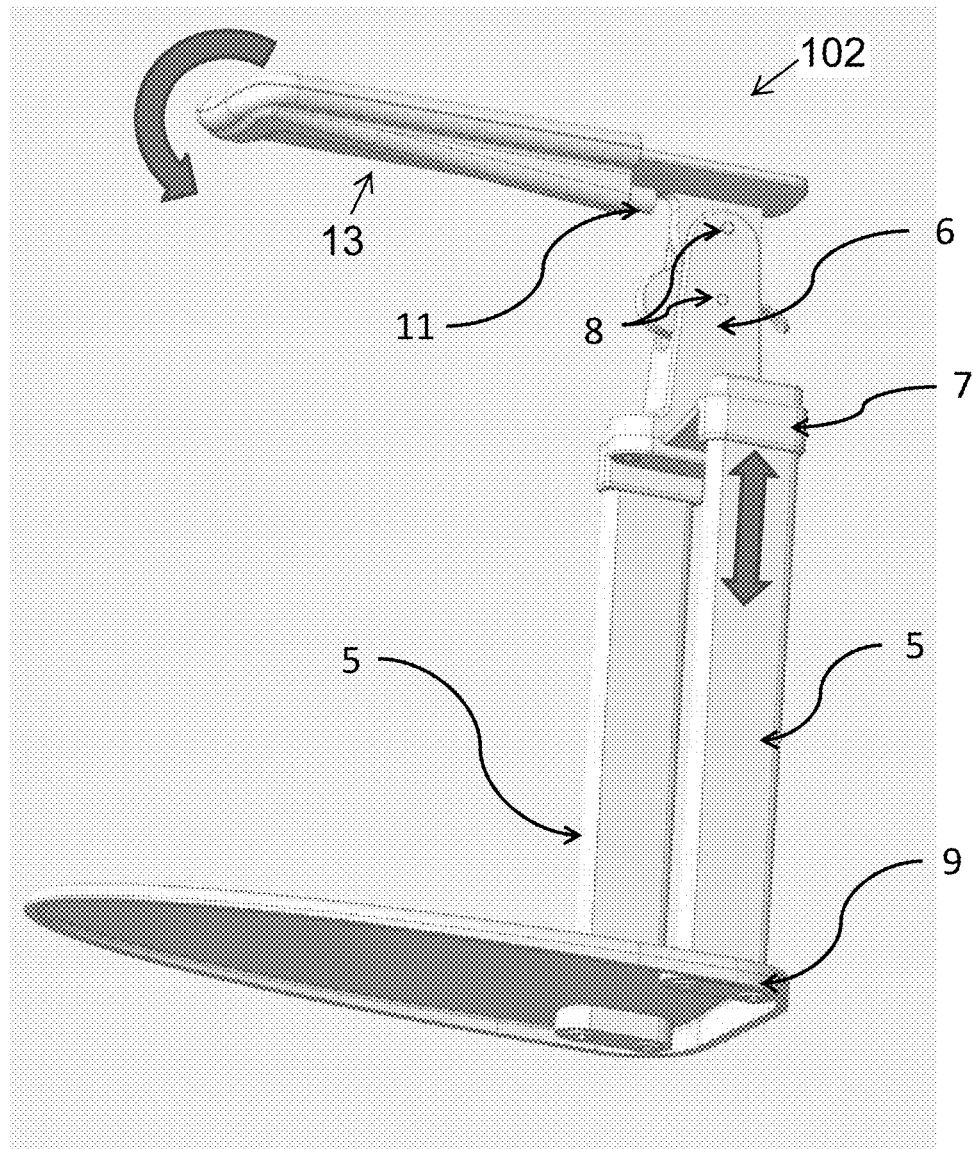
FIG. 7 shows an isometric view of an exemplary system looking from the bottom up wherein the blade is extended and at the top most position on the supports indicating the rotational angle of the blade motion, according to some aspects.

As shown in at least FIG. 4, in some aspects, the movable blade 1 may include an internal cavity with small openings 10 near the front edge and, as shown in FIG. 7, a suction connection 11 on the rear edge to connect to standard medical vacuum tubing. In some aspects, the suction connection 11 provides suction to remove surgical and bodily fluids present during operation.

Figure 5:
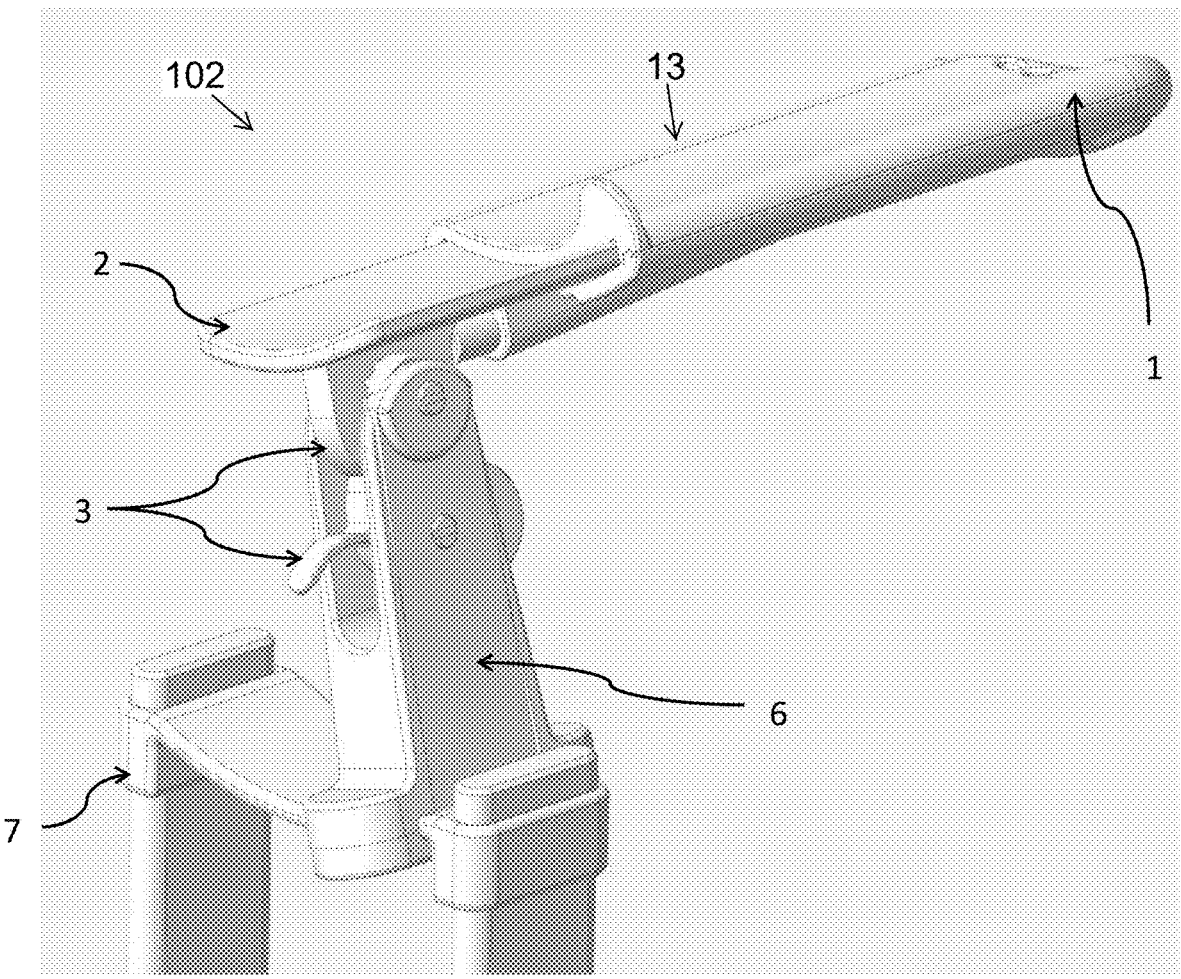
FIG. 5 shows a close-up isometric view of an exemplary system wherein the blade is extended, the ratchet back side in view, and the blade assembly is pivoted, according to some aspects.
Figure 6:
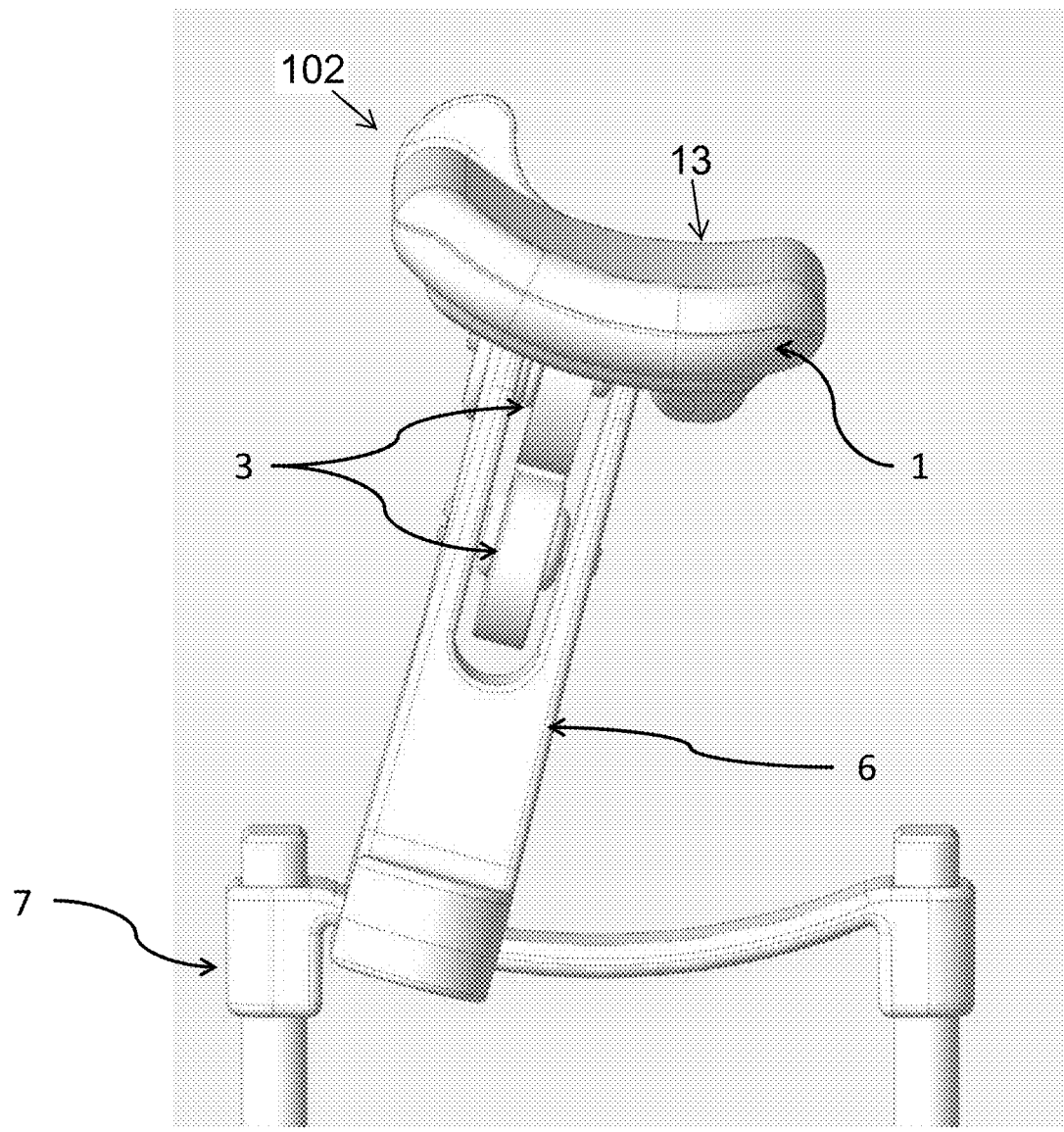
FIG. 6 shows a close-up front view of an exemplary system wherein the blade is at the top most position on the supports and the blade assembly is pivoted, according to some aspects.

As shown in at least FIGS. 5 and 6, in some aspects, the retractor 102 may include a slider track 7 (e.g., a curved slider track), which allows the blade assembly 13 to pivot from side to side, improving access to the side walls of the vaginal canal.

Figure 8:
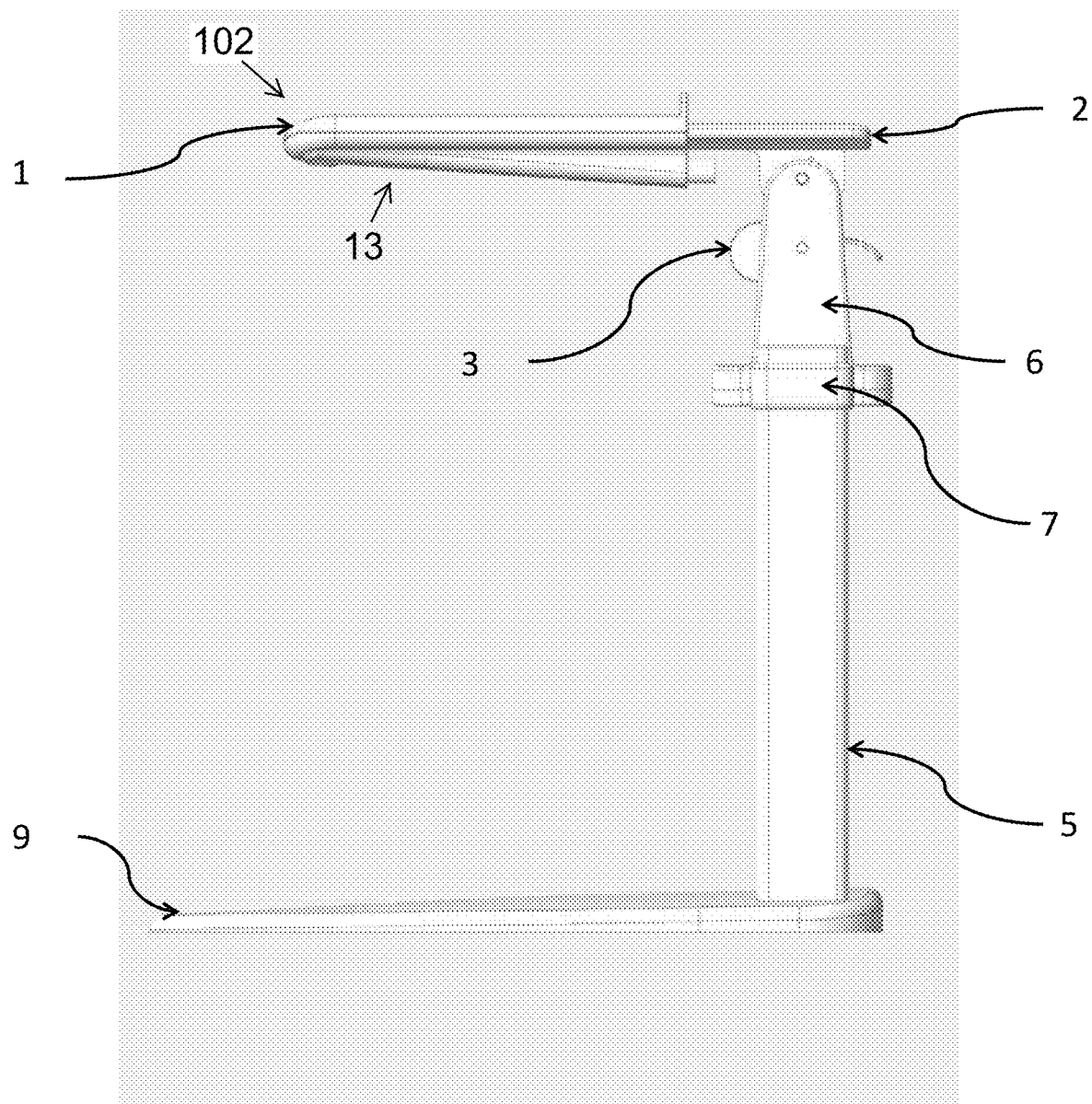
FIG. 8 shows a side view of an exemplary system wherein the blade is at the top most position on the supports, according to some aspects.
Figure 13:
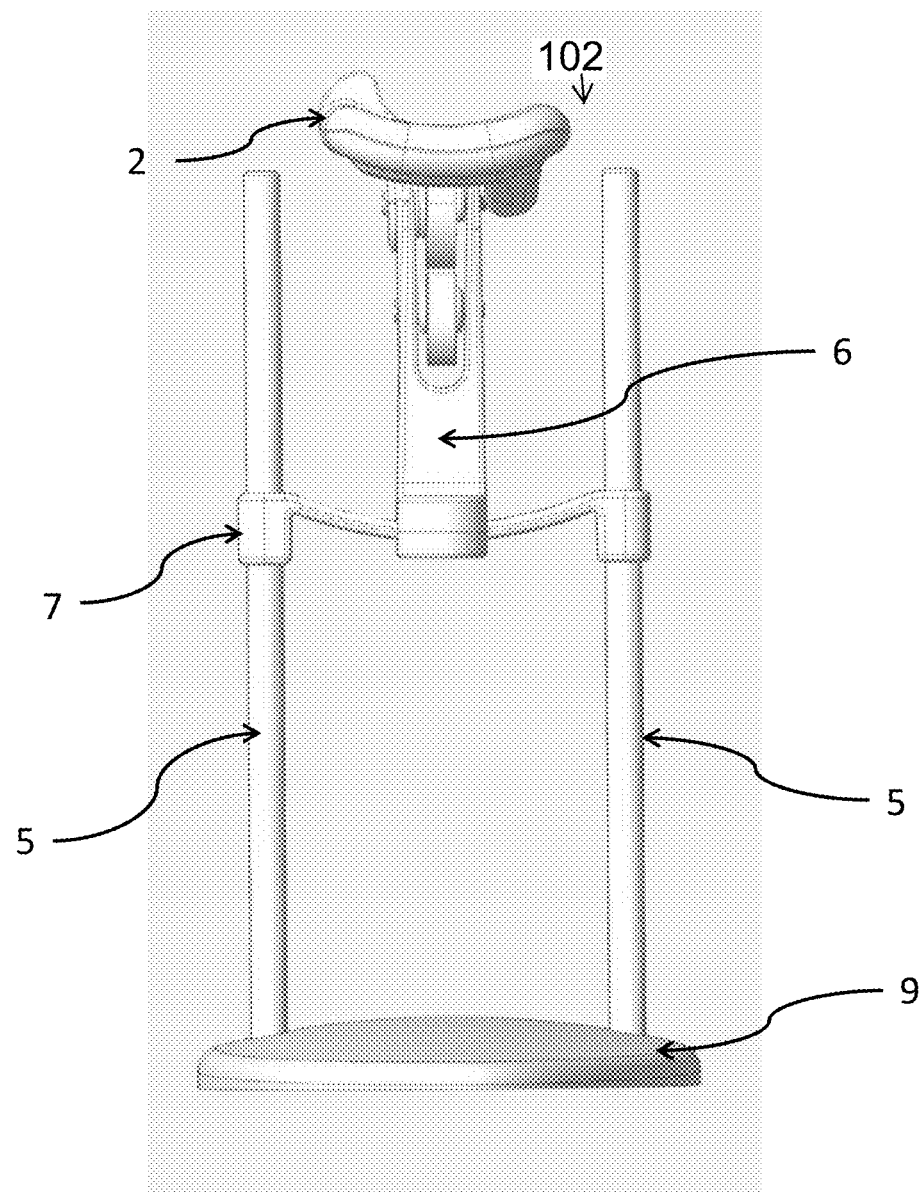
FIG. 13 shows a front view of an exemplary system wherein the blade is at the middle position on the supports, according to some aspects.
Figure 14:
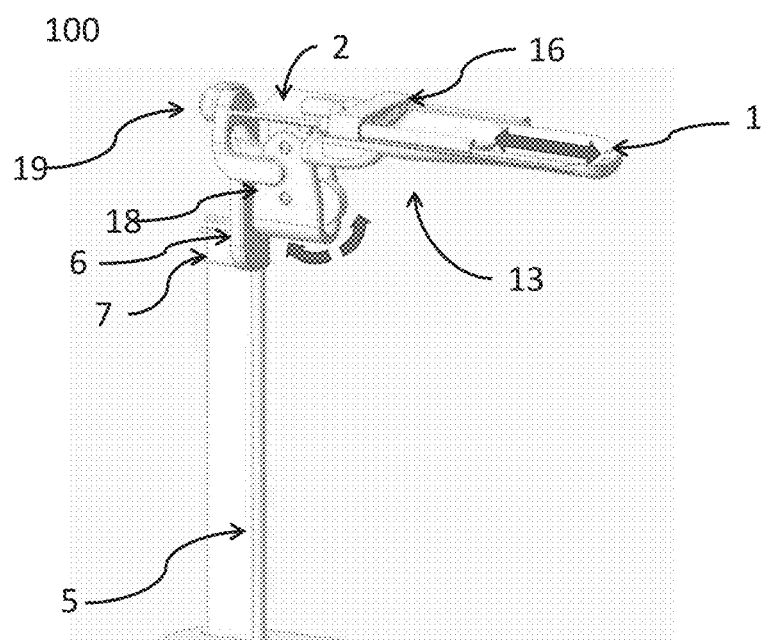
FIG. 14 shows an isometric view of another aspect of an exemplary system that uses a pivoting mechanism and support structure to enable 360 degree rotation of the blade assembly, according to some aspects.
Figure 15:
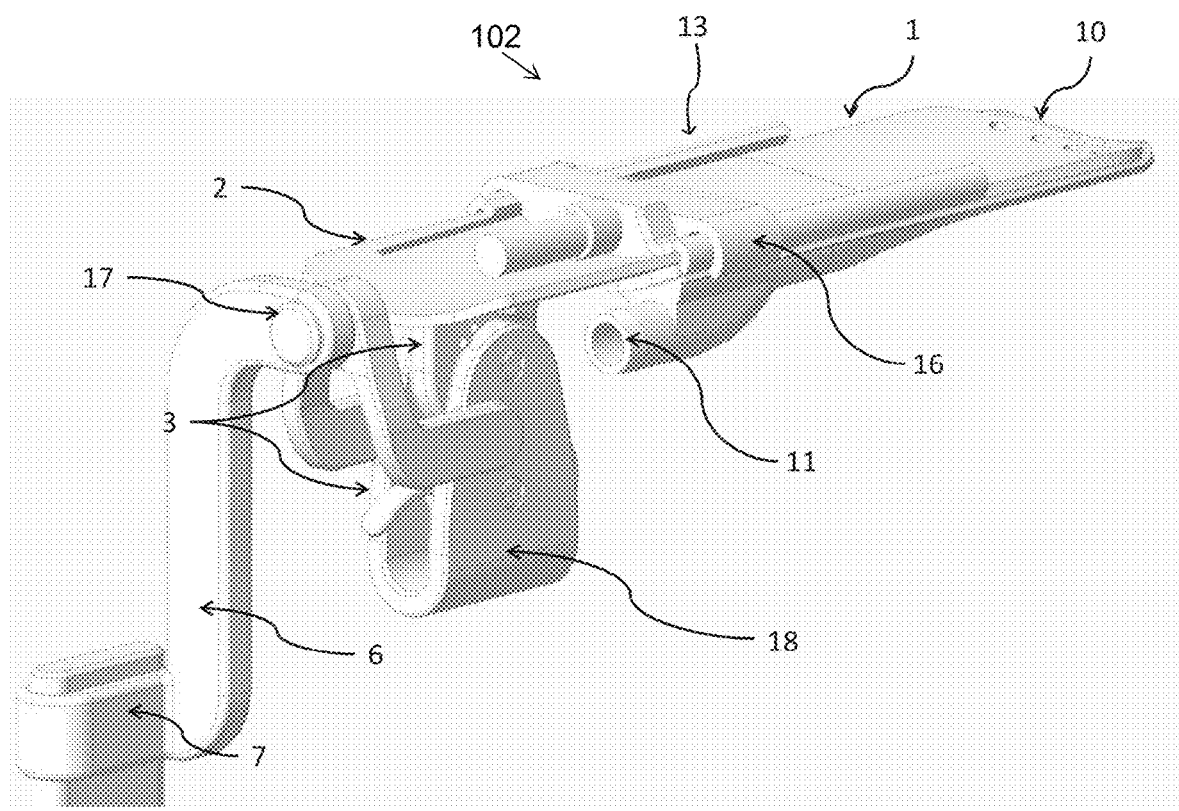
FIG. 15 shows a close-up isometric view of another aspect of an exemplary system wherein the blade is extended and the ratchet back side in view, according to some aspects.
Figure 16:
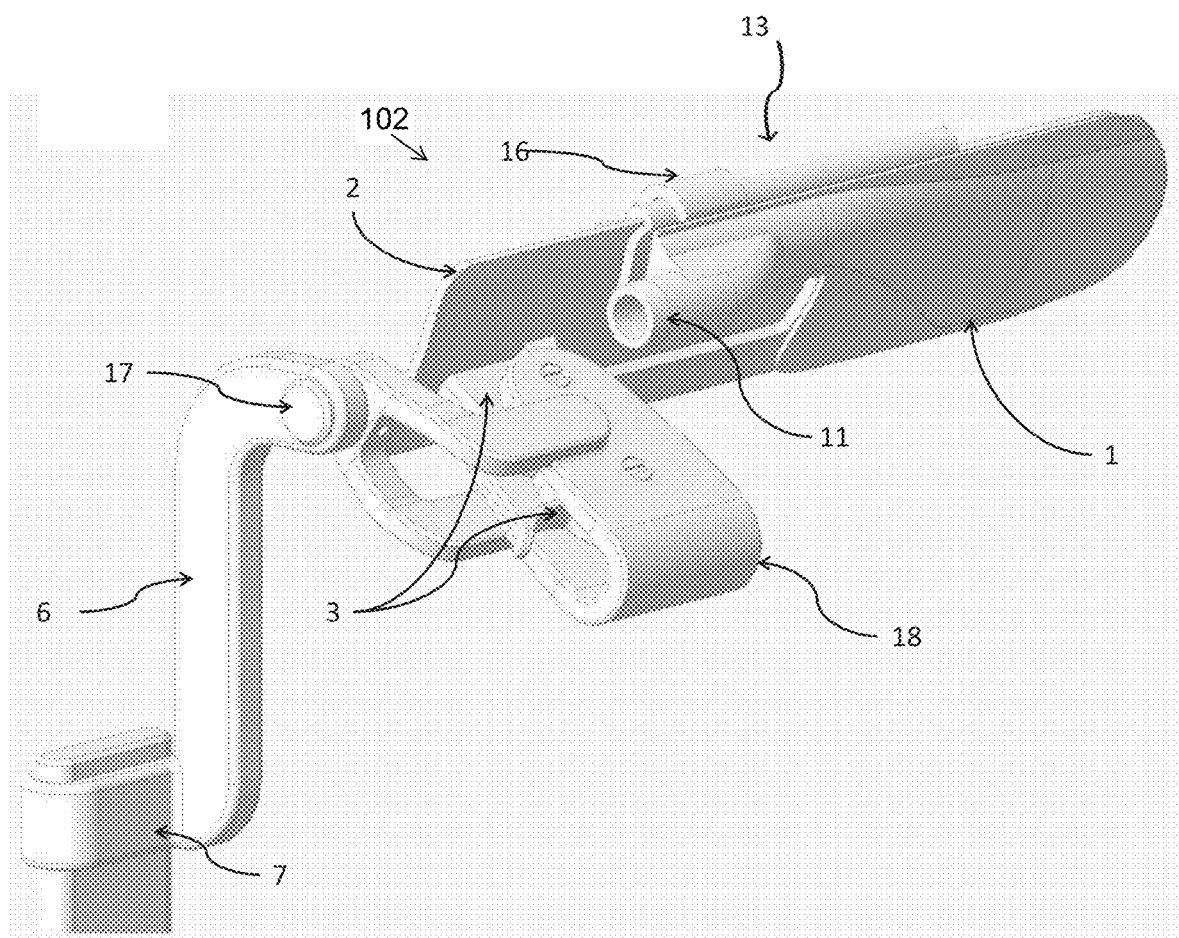
FIG. 16 shows a close-up isometric view of another aspect of an exemplary system wherein the blade is extended, the ratchet back side in view, and the blade assembly is pivoted, according to some aspects.
Figure 17:
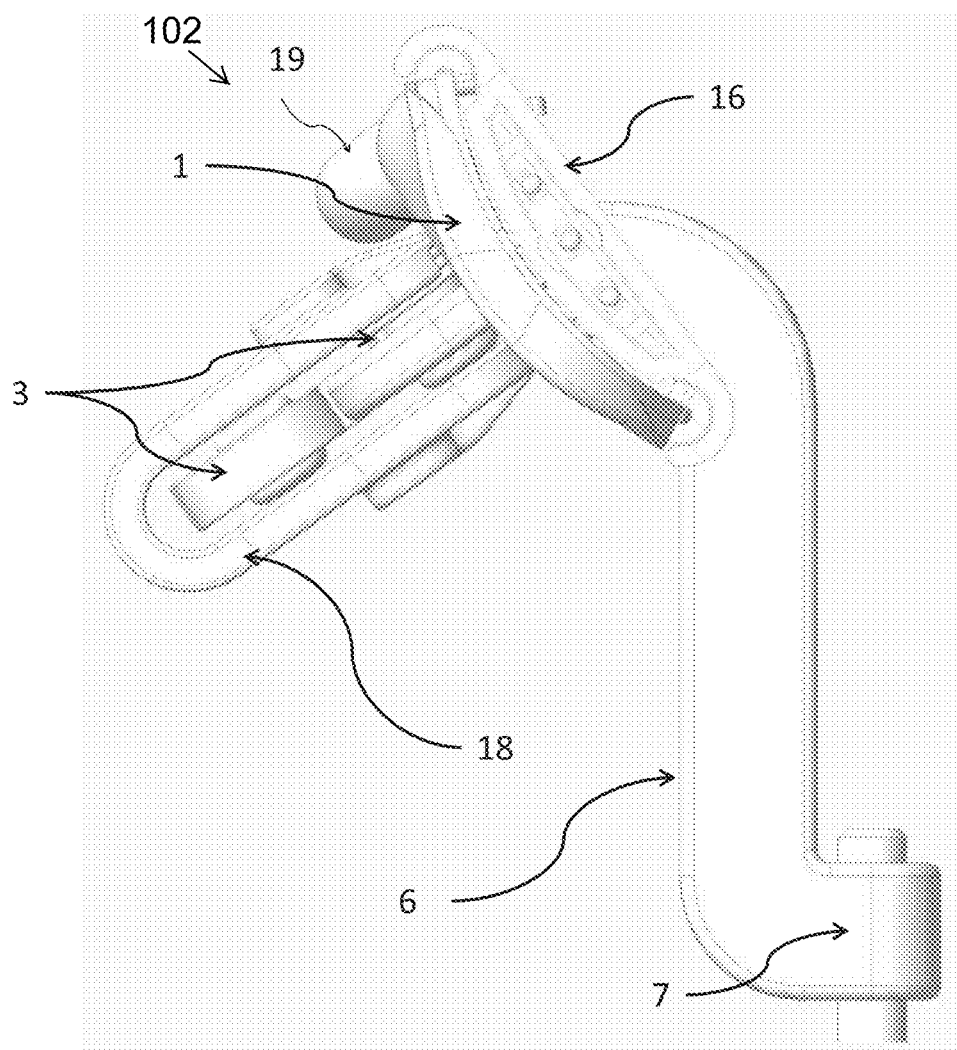
FIG. 17 shows a close-up view of another aspect of an exemplary system wherein the blade assembly is pivoted, according to some aspects.

As shown in at least FIGS. 7, 8, and 13, in some aspects, the blade 2 and ratchet parts 3 may be assembled into the slider 6 parts with one or more screws 8 (identified in FIG. 7), which will allow the blade assembly 13 to travel up and down along one or more supports 5. In some aspects, and as shown in at least FIG. 7, the slider track 7 may slide along the one or more supports 5, which may allow for height adjustment of the retractor 102 from the surface of, for example, an operating table to the posterior angle of the vaginal opening. In FIGS. 7 and 8, the retractor 102 is shown as having been moved to an upper position on the one or more supports 5. In FIG. 13, the retractor 102 is shown as having been moved to a lower position on the one or more supports 5 by the slider track 7.

Figure 9:
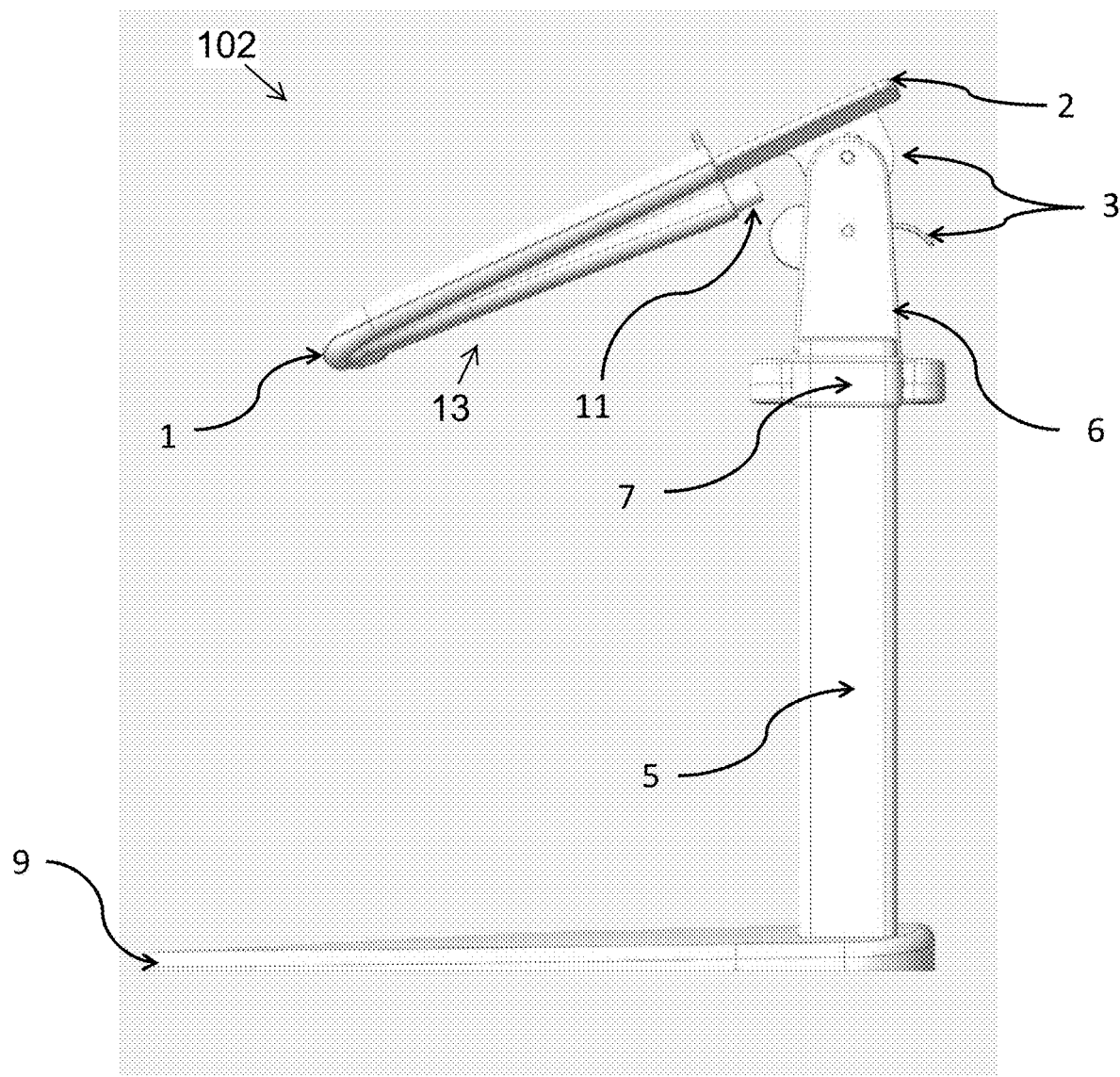
FIG. 9 shows a side view of an exemplary system wherein the blade is on an angle and at the top most position on the supports, according to some aspects.
Figure 10:
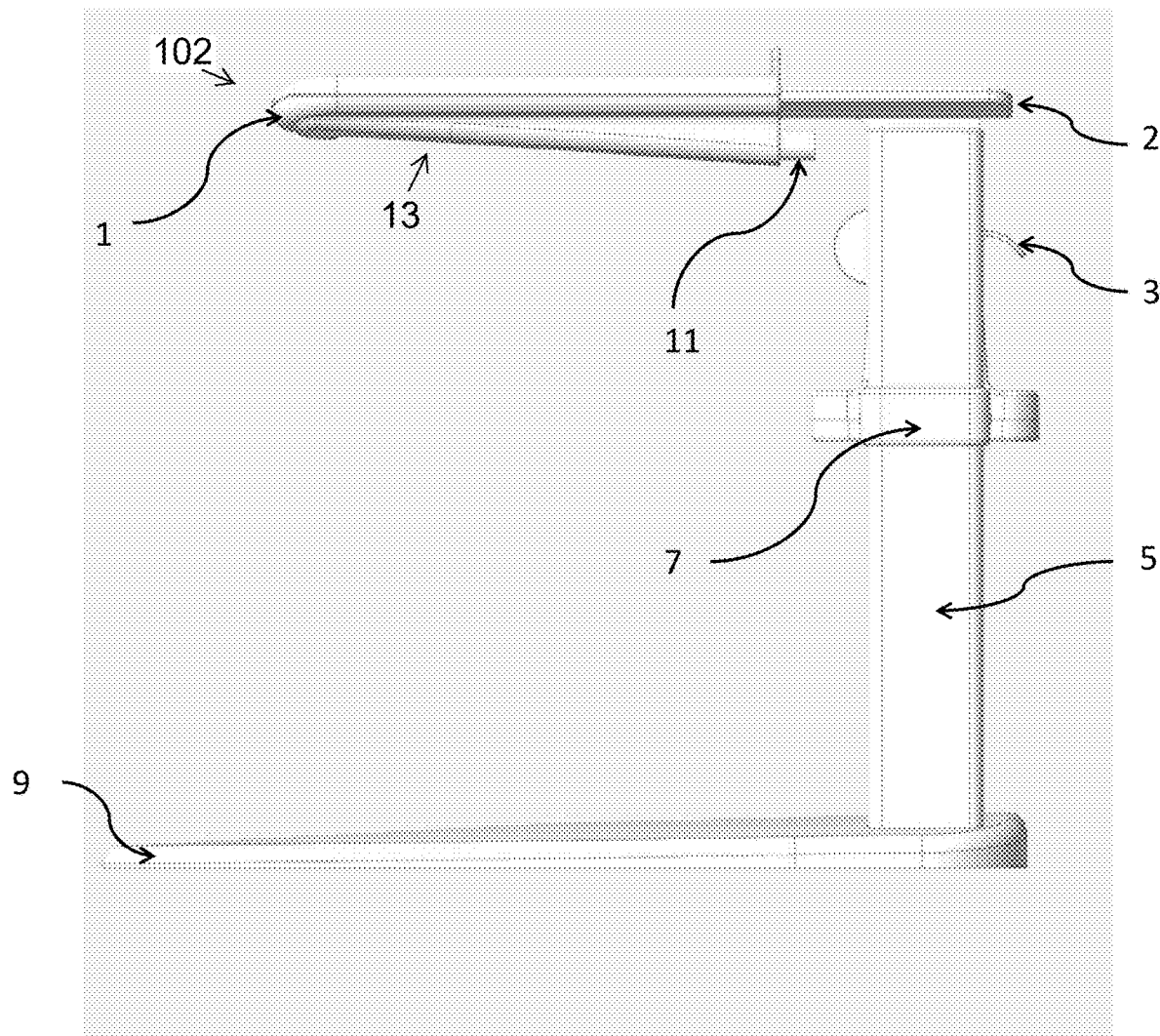
FIG. 10 shows a side view of an exemplary system wherein the blade is at the bottom most position on the supports, according to some aspects.
Figure 11:
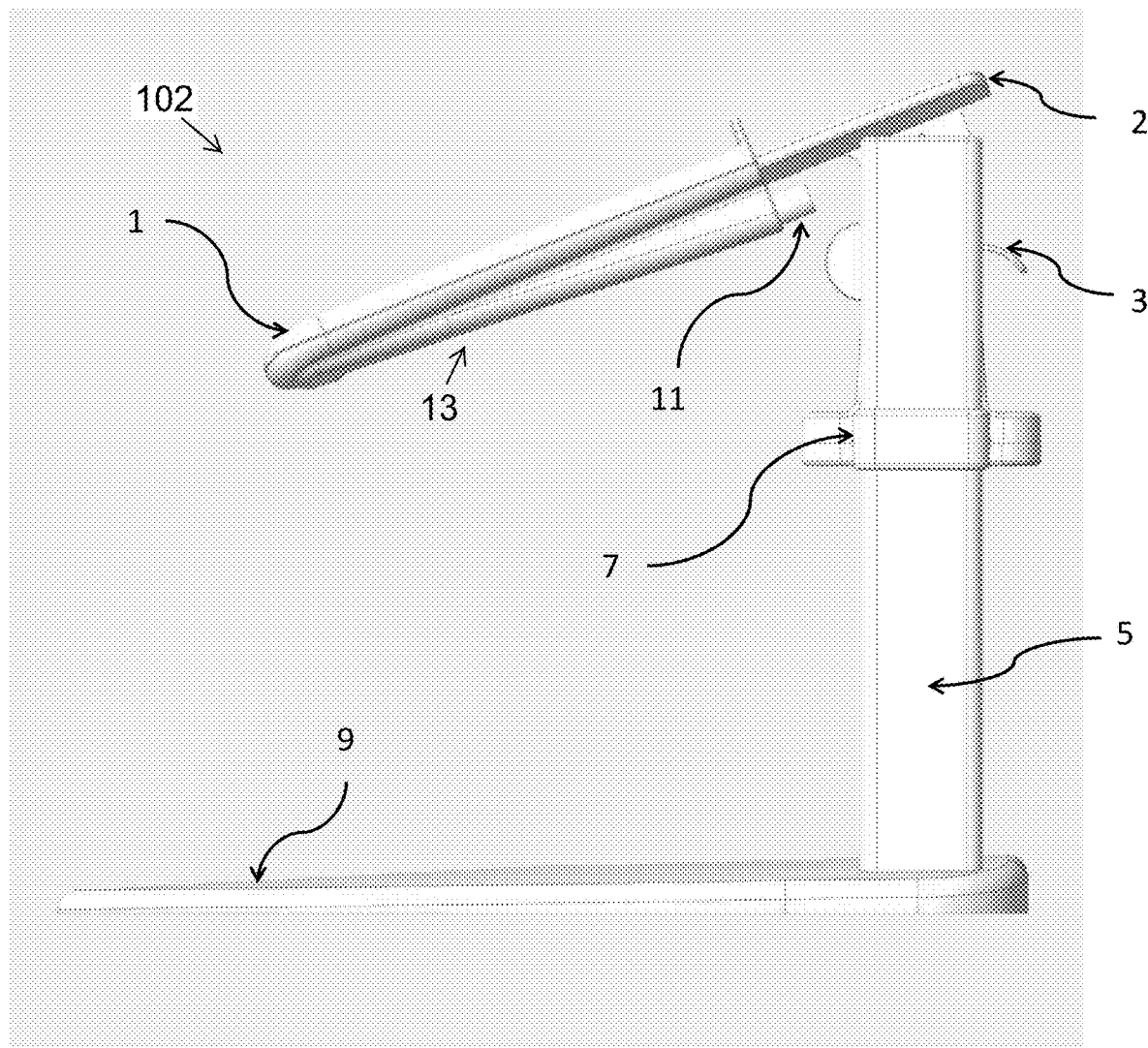
FIG. 11 shows a side view of an exemplary system wherein the blade is on an angle and at the bottom most position on the supports, according to some aspects.

As shown in at least FIGS. 9, 10, and 11, in some aspects, the blade assembly 13 may be pitched, by means of the ratchet parts 3, up and down, for example, to enable improved access to the vaginal canal. In some aspects, the system 100 may have the blade assembly 13 pitched, by means of the ratchet parts 3, and also moved up and down the one or more supports 5, by means of the slider track 7.

Figure 12:
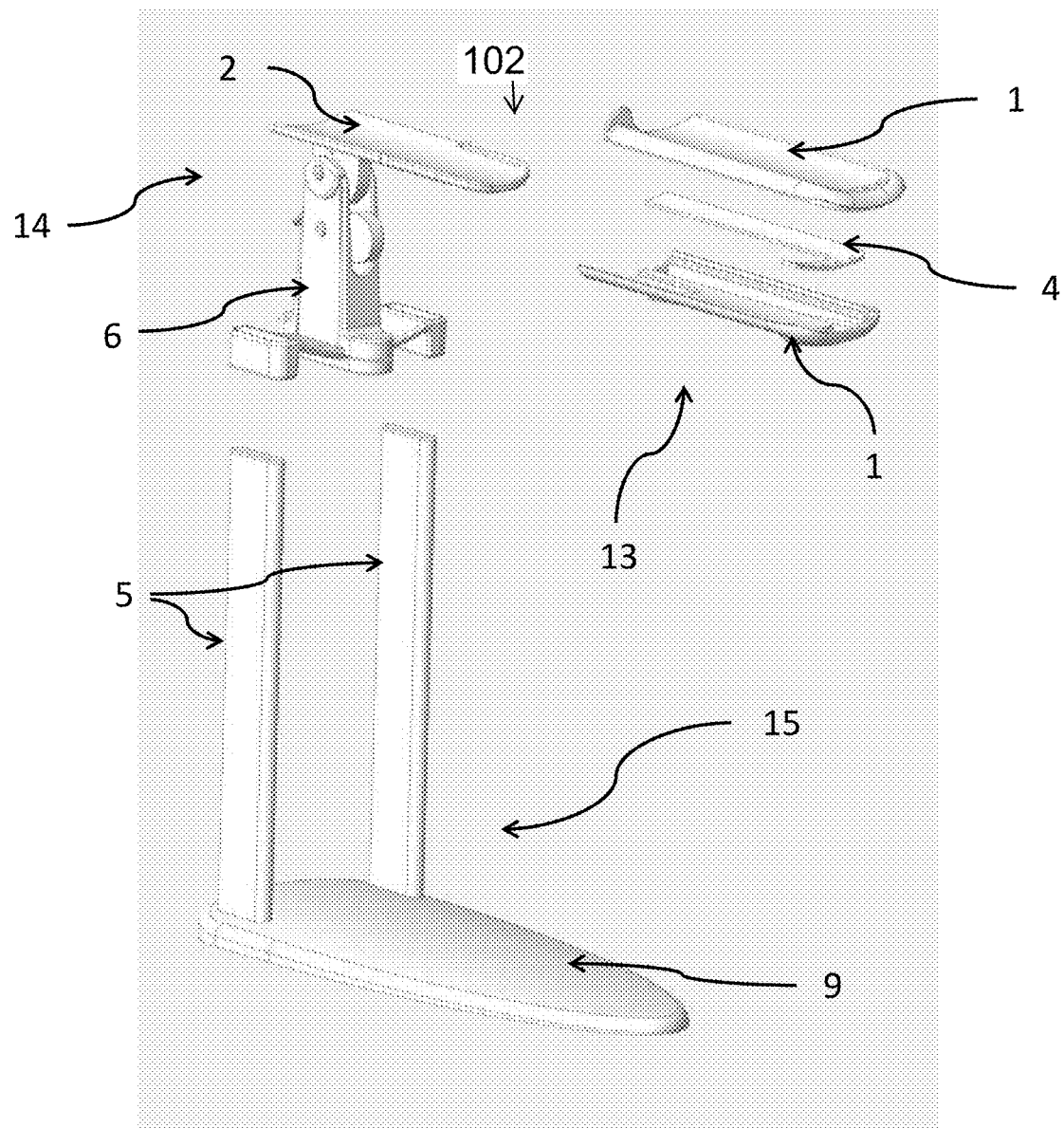
FIG. 12 shows an exploded view of an exemplary system indicating the three main assemblies, according to some aspects.

As shown in FIG. 12, in some aspects, the retractor 102 may have multiple assemblies, including, for example and without limitation, a blade assembly 13, a ratchet assembly 14, and a base assembly 15.

FIGS. 14-17 illustrate the retractor 102 according to some alternative aspects. In some aspects, as shown in FIGS. 14-17, the retractor 102 may include a pivoting mechanism 19, a pivot connection 17, a light track 16, and a support structure 18. In some aspects, the pivot mechanism 19 may allow the blade assembly 13 to pivot (e.g., pivot 360 degrees). In some aspects, the pivot mechanism 19, pivot connection 17, light track 16, and support structure 18 may allow for the retractor 102 to have improved access to the vaginal canal.

In addition, in some aspects, all the parts of the retractor 102 may be made out of plastic and/or metal (e.g., stainless steel). In some aspects, the retractor 102 may be single use, which may help to minimize the sterilization process and/or rate of infection.

In some aspects, the retractor 102 may adjust to the exact vaginal depth and to the individual posterior vaginal angle. In some aspects, the blades may be rotated for maximum exposure. In some aspects, the suction chamber in the extension blade may allow for a surgical field free of smoke during fulguration and elimination of blood pooling. In some aspects, the retractor 102 may include lighting. In some aspects, the retractor 102 may be self-retaining, may adjust for variable vaginal depths, may adjust for variable posterior vaginal angle, and/or may adjust for increased access to the side walls, thus allowing for maximum exposure of the canal. However, in some alternative aspects, a different retractor 102 (e.g., a retractor 102 that does not adjust for various vaginal depths and/or does not adjust for increased access to side walls) may be used with the holder 104. For example, in some aspects, the holder 104 may be used with a retractor 102 having a fixed blade length and/or a fixed angle between the blade and stem or supports.

Figure 18:
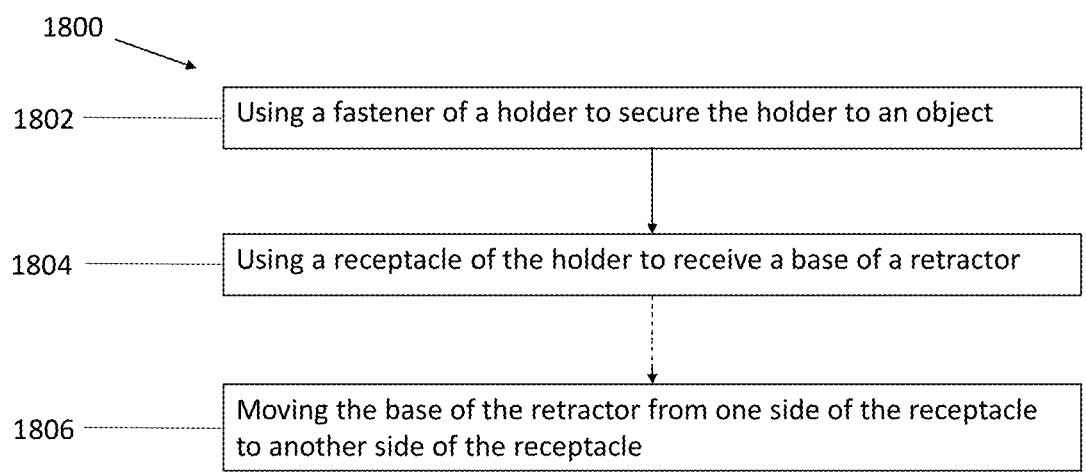
FIG. 18 is a flowchart illustrating a process according to some aspects.

FIG. 18 illustrates a process 1800 according to some aspects. In some aspects, as shown in FIG. 18, the process 1800 may include a step 1802 of using a fastener 20 of a holder 104 to secure the holder 104 to an object. In some aspects, as shown in FIG. 18, the process 1800 may include a step 1804 of using a receptacle 12 of the holder 104 to receive a base 9 of a retractor 102. In some aspects, as shown in FIG. 18, the process 1800 may include an optional step 1806 of moving the base 9 of the retractor 102 from one side of the receptacle 12 to another side of the receptacle 12. In some aspects (e.g., some aspects in which the retractor 102 is a vaginal speculum), the process 1800 may additionally include one or more of (i) extending the movable blade 1 of the retractor 102 to match a patient's depth of the vagina, (ii) adjusting the height of the blade assembly 13 such that the blades lie on the surface of the posterior wall of the vagina, (iii) using the blade angle mechanism (e.g., ratchet assembly 14 including spring-loaded ratchet parts 3) and/or the blade pivoting mechanism (e.g., slider 6 and slider track 7 or pivot connection 17) to achieve optimal exposure without undue pressure against the vaginal wall, and/or (iv) after reaching the maximal achievable exposure without undue pressure on the posterior wall, using the ratchet assembly 14 to keep the blade in this fixed position.

While various aspects are described herein, it should be understood that they have been presented by way of example only, and not limitation. Thus, the breadth and scope of this disclosure should not be limited by any of the above-described exemplary aspects. Moreover, any combination of the above-described elements in all possible variations thereof is encompassed by the disclosure unless otherwise indicated herein or otherwise clearly contradicted by context.

The invention claimed is:

1. A system comprising:
   a retractor including:
      a blade assembly;
      a base; and
      one or more supports attached to the base and the blade assembly; and
   a holder including:
      a receptacle configured to receive the base, wherein the receptacle comprises:
         a front end;
         a bottom surface;
         a top surface;
         a cavity defined by at least the front end, the bottom surface, and the top surface; and
         an opening to the cavity at a rear end of the receptacle, wherein the rear end is opposite the front end;
         wherein the top surface comprises a recess at the rear end, and the receptacle is configured such that, when the base of the retractor is received by the receptacle, at least a portion of the base of the retractor is within the cavity, and the one or more supports of the retractor pass through the recess in the top surface of the receptacle; and a clip on the top surface of the receptacle, wherein the clip is configured to secure the holder to an object.

2. The system of claim 1, wherein the receptacle is configured to prevent rotation of the base about a longitudinal axis of the base.

3. The system of claim 1, wherein the holder is configured to maintain the base of the retractor at a constant height.

4. The system of claim 1, wherein the holder is configured to maintain a longitudinal axis of the one or more supports in a vertical orientation.

5. The system of claim 1, wherein the receptacle is made of plastic.

6. The system of claim 1, wherein the receptacle of the holder is configured such that the base of the retractor is capable of side-to-side movement within the receptacle.

7. The system of claim 1, wherein the object is an operating room table.

8. The system of claim 1, wherein the one or more supports comprise one or more columns.

9. The system of claim 1, wherein the retractor is a speculum.

10. A holder comprising:
    a receptacle comprising:
        a front end;
        a bottom surface;
        a top surface;
        a cavity defined by at least the front end, the bottom surface, and the top surface; and
        an opening to the cavity at a rear end of the receptacle, wherein the rear end is opposite the front end;
        wherein the top surface comprises a recess at the rear end; and
    a clip on the top surface of the receptacle, wherein the clip is configured to secure the receptacle to an object.

11. The holder of claim 10, wherein the receptacle is configured to receive a base of a retractor, the retractor comprises one or more supports attached to the base, and the receptacle is configured such that, when the base of the retractor is received by the receptacle, at least a portion of the base of the retractor is within the cavity, and the one or more supports of the retractor pass through the recess in the top surface of the receptacle.

12. The holder of claim 11, wherein the holder is configured to maintain the base of the retractor at a constant height.

13. The holder of claim 11, wherein the holder is configured to maintain a longitudinal axis of the one or more supports in a vertical orientation.

14. The holder of claim 10, wherein the object is an operating room table.

15. The holder of claim 11, wherein the receptacle of the holder is configured such that the base of the retractor is capable of side-to-side movement within the cavity of the receptacle.

16. The holder of claim 11, wherein the receptacle is configured to prevent rotation of the base about a longitudinal axis of the base.

17. The holder of claim 11, wherein the receptacle is configured such that, when the base of the retractor is received by the receptacle, the one or more supports of the retractor abut a front edge of the recess in the top surface of the receptacle.

18. The holder of claim 17, wherein the receptacle is configured such that, when the base of the retractor is received by the receptacle, the one or more supports of the retractor abut the clip.

19. The holder of claim 10, wherein the front end of the receptacle is tapered.

20. The holder of claim 10, wherein the clip abuts the recess in the top surface of the receptacle.

21. A method comprising:
    using a clip on a top surface of a receptacle of a holder to secure the holder to an object; and
    using the receptacle of the holder to receive a base of a retractor, wherein the receptacle comprises:
        a front end;
        a bottom surface;
        a top surface;
        a cavity defined by at least the front end, the bottom surface, and the top surface; and
        an opening to the cavity at a rear end of the receptacle, wherein the rear end is opposite the front end;
    wherein the top surface comprises a recess at the rear end, and, when the base of the retractor is received by the receptacle, at least a portion of the base of the retractor is within the cavity, and one or more supports of the retractor that are attached to the base of the retractor pass through the recess in the top surface of the receptacle.

22. The method of claim 21, further comprising moving the base of the retractor from one side of the receptacle to another side of the receptacle.

* * * * *